US011719092B2

(12) United States Patent
Katterbauer et al.

(10) Patent No.: US 11,719,092 B2
(45) Date of Patent: Aug. 8, 2023

(54) SYSTEMS AND METHODS FOR DRILLING A WELLBORE USING TAGGANT ANALYSIS

(71) Applicant: SAUDI ARABIAN OIL COMPANY, Dhahran (SA)

(72) Inventors: Klemens Katterbauer, Dhahran (SA); Alberto Marsala, Venice (IT); Nouf Jabri, Dhahran (SA); Martin E. Poitzsch, Northumberland, NH (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 358 days.

(21) Appl. No.: 17/069,080

(22) Filed: Oct. 13, 2020

(65) Prior Publication Data
US 2022/0112801 A1    Apr. 14, 2022

(51) Int. Cl.
*E21B 47/11* (2012.01)
*E21B 47/04* (2012.01)
*E21B 49/00* (2006.01)
*G01N 33/28* (2006.01)

(52) U.S. Cl.
CPC .............. *E21B 47/11* (2020.05); *E21B 47/04* (2013.01); *E21B 49/005* (2013.01); *G01N 33/2823* (2013.01); *E21B 2200/20* (2020.05)

(58) Field of Classification Search
CPC ............................. E21B 47/11; E21B 2200/20
See application file for complete search history.

(56) References Cited

U.S. PATENT DOCUMENTS

| 6,840,316 | B2 | 1/2005 | Stegemeier et al. |
| 8,172,007 | B2 | 5/2012 | Dolman et al. |
| 8,610,431 | B2 | 12/2013 | Chen et al. |
| 8,627,902 | B2 * | 1/2014 | Hammer ................. E21B 21/08 175/42 |
| 8,628,902 | B2 | 1/2014 | Yamasaki et al. |
| 10,041,844 | B1 | 8/2018 | Brady et al. |

(Continued)

FOREIGN PATENT DOCUMENTS

| CN | 108930535 A | 12/2018 |
| CN | 110965991 A | 4/2020 |

(Continued)

OTHER PUBLICATIONS

International Search Report and Written Opinion of the International Searching Authority issued in corresponding International Application No. PCT/US2021/054729 dated Feb. 8, 2022 (15 pages).

(Continued)

Primary Examiner — Tara Schimpf
(74) Attorney, Agent, or Firm — Osha Bergman Watanabe & Burton LLP

(57) ABSTRACT

A system for drilling a wellbore is disclosed. The injection pump releases the taggant into the mud stream traveling downhole. The taggant attaches to the rock cuttings and it is detected on the surface by the taggant detector. The taggant detector provides the data relating to the taggants detected in the drilling fluid. The data is analyzed by taggant analysis and control engine, which produces an injection profile. Based on the injection profile, the IoT Controller adapts the parameters of the taggant injection pump to achieve a real-time optimization of the taggant injection.

18 Claims, 8 Drawing Sheets

(56) References Cited

U.S. PATENT DOCUMENTS

| | | |
|---|---|---|
| 2009/0087911 A1 | 4/2009 | Ramos |
| 2009/0087912 A1 | 4/2009 | Ramos et al. |
| 2010/0015612 A1 | 1/2010 | Pelham et al. |
| 2012/0178653 A1 | 7/2012 | McClung, III |
| 2016/0146002 A1 | 5/2016 | Walls et al. |
| 2019/0360326 A1 | 11/2019 | Deville et al. |
| 2019/0368336 A1 | 12/2019 | Hammond |
| 2020/0116019 A1 | 4/2020 | Ow et al. |
| 2020/0277852 A1* | 9/2020 | Smithson ............... E21B 47/11 |
| 2021/0254449 A1 | 8/2021 | Wei et al. |

FOREIGN PATENT DOCUMENTS

| | | |
|---|---|---|
| WO | 2012115717 A2 | 8/2012 |
| WO | 2016016335 A1 | 2/2016 |
| WO | 2020014300 A1 | 1/2020 |
| WO | 2020/081426 A1 | 4/2020 |
| WO | 2020089587 A1 | 5/2020 |

OTHER PUBLICATIONS

Poitzsch, Martin E. et al., "IPTC-19785 Nanoparticle Tags for Improved Depth Correlation", Saudi Aramco, International Petroleum Technology Conference 2020, Jan. 2020 (15 pages).

* cited by examiner

SYSTEMS AND METHODS FOR DRILLING A WELLBORE USING TAGGANT ANALYSIS

BACKGROUND

A taggant is used in oil and gas industry for many years. It has been used to impart a detectable signature into a fluid. Tracking the fluid, marked with the taggant, provides information about a well property or condition. The taggant is commonly used by being injected into the well and by being detected in the adjacent formation or in an adjacent well. The presence of a particular taggant in the adjacent formation or in the adjacent well enables understanding a precise position of wellbores and enables assessments of the wells.

SUMMARY

In general, in one aspect, the invention relates to a system for drilling a wellbore. The system includes a drill string disposed in the wellbore, the drill string having a central aperture and defining an annulus between the drill string and side walls of the wellbore, a taggant injection pump in fluid communication with a circulation path for a drilling fluid and configured to selectively inject taggants into the drilling fluid, an IoT controller arranged to control the taggant injection pump, a taggant detector in fluid communication with a return part of the circulation path, the taggant detector producing information relating to the taggants detected in the drilling fluid and a taggant analysis and control engine that receives the information from the taggant detector, analyzes the information in real time, and provides instructions to the IoT controller to improve a quality of the rock cutting depth determination, wherein mud logging is performed based on the improved quality of the rock cutting depth determination.

In general, in one aspect, the invention relates to a method for drilling a wellbore. The method includes generating, using a machine learning model and based on a drilling fluid parameter, a drilling parameter, and a formation parameter, to generate an injection profile, controlling, based on the injection profile, injection parameters of a taggant injection pump to improve a quality of rock cutting depth determination, wherein the taggant injection pump is in fluid communication with a circulation path for a drilling fluid, releasing, using the taggant injection pump, taggants into the drilling fluid, wherein the taggants are transported downhole by the drilling fluid to impregnate rock cuttings as the rock cuttings are produced by a drill bit, detecting, using a taggant detector in fluid communication with a return part of the circulation path, the taggants for determining a rock cutting depth of the rock cuttings, wherein mud logging is performed based on the improved quality of the rock cutting depth determination.

In general, in one aspect, the invention relates to a non-transitory computer readable medium storing instructions, that when executed, are configured to perform a method rock cutting depth determination. The instructions, when executed, include functionality generating, using a machine learning model and based on a drilling fluid parameter, a drilling parameter, and a formation parameter, to generate an injection profile, controlling, based on the injection profile, injection parameters of a taggant injection pump to improve a quality of rock cutting depth determination, wherein the taggant injection pump is in fluid communication with a circulation path for a drilling fluid, releasing, using the taggant injection pump, taggants into the drilling fluid, wherein the taggants are transported downhole by the drilling fluid to impregnate rock cuttings as the rock cuttings are produced by a drill bit, detecting, using a taggant detector in fluid communication with a return part of the circulation path, the taggants for determining a rock cutting depth of the rock cuttings, wherein mud logging is performed based on the improved quality of the rock cutting depth determination.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
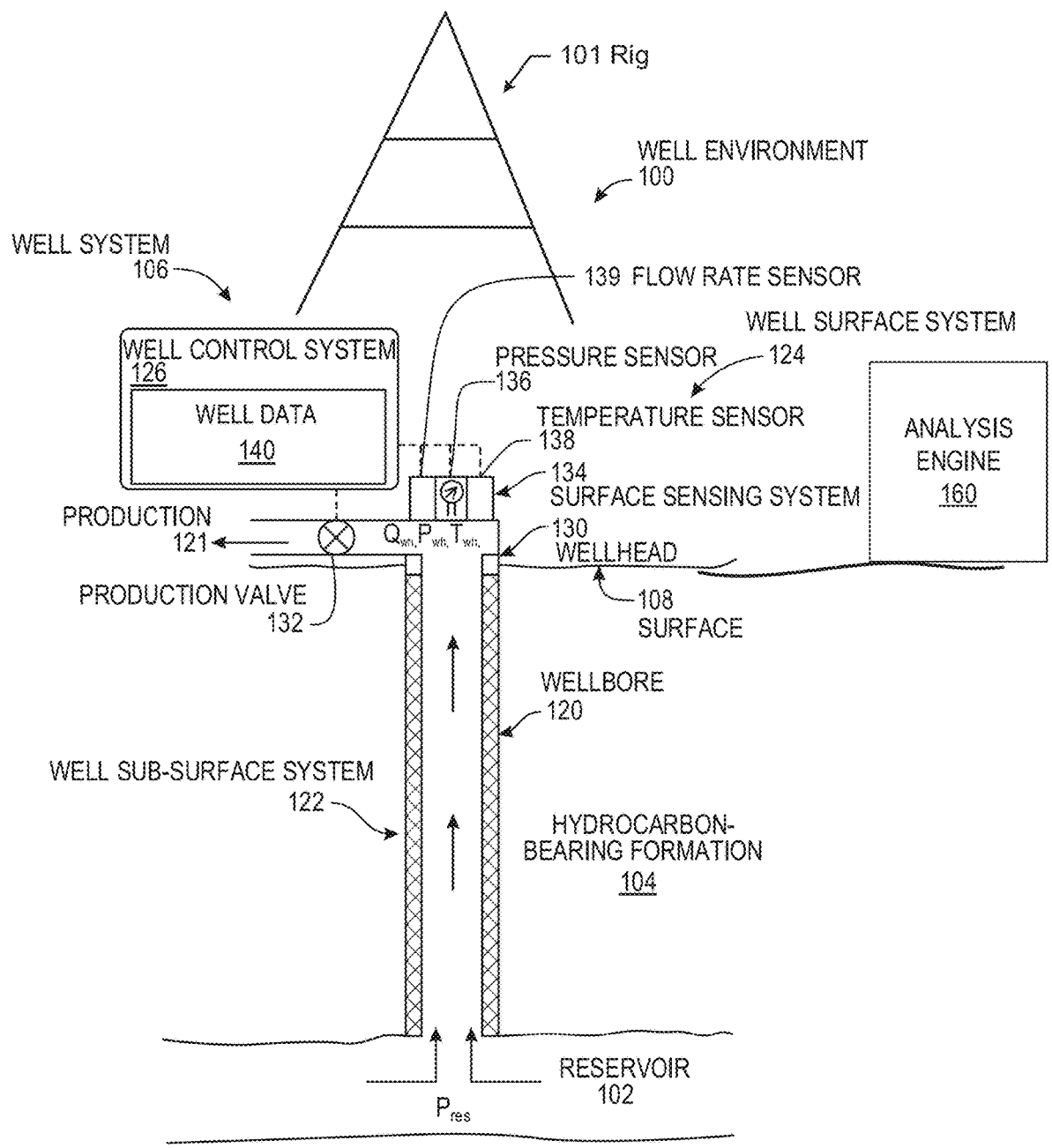
FIGS. 1 and 2 show systems in accordance with one or more embodiments

Specific embodiments disclosed herein will now be described in detail with reference to the accompanying figures. Like elements in the various figures are denoted by like reference numerals for consistency. Like elements may not be labeled in all figures for the sake of simplicity.

In the following detailed description of embodiments disclosed herein, numerous specific details are set forth in order to provide a more thorough understanding disclosed herein. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-5, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that, one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

One or more embodiments are directed towards a system, a method and a non-transitory computer readable medium for drilling a wellbore using tagged objects, called nanotags. Nanotags may comprise any suitable taggant which enables detection within the selected system. For example, nanotags may be chemical markers, radioactive isotope markers, ferroelectric markers, optical isomers markers, etc.

FIG. 1 shows a schematic diagram in accordance with one or more embodiments. As shown in FIG. 1, a well environment (100) includes a hydrocarbon reservoir ("reservoir") (102) located in a subsurface hydrocarbon-bearing formation ("formation") (104) and a well system (106). The hydrocarbon-bearing formation (104) may include a porous or fractured rock formation that resides underground, beneath the earth's surface ("surface") (108). In the case of the well system (106) being a hydrocarbon well, the reservoir (102) may include a portion of the hydrocarbon-bearing formation (104). The hydrocarbon-bearing formation (104) and the reservoir (102) may include different layers of rock having varying characteristics, such as varying degrees of permeability, porosity, capillary pressure, and resistivity. In the case of the well system (106) being operated as a production well, the well system (106) may facilitate the extraction of hydrocarbons (or "production") from the reservoir (102).

In some embodiments of the invention, the well system (106) includes a rig (101), a wellbore (120), a well subsurface system (122), a well surface system (124), and a well control system ("control system") (126). The well control system (126) may control various operations of the well system (106), such as well production operations, well drilling operation, well completion operations, well maintenance operations, and reservoir monitoring, assessment and development operations. In some embodiments, the well control system (126) includes a computer system that is the same as or similar to that of a computer system (500) described below in FIGS. 5A and 5B and the accompanying description. For example, the taggant detector (201), the IoT controller (203), and the taggant injection pump (204) depicted in FIG. 2 below may be part of the well control system (126) and may be implemented as a combination of hardware and software components of the computer system (500).

The rig (101) is the machine used to drill a borehole to form the wellbore (120). Major components of the rig (101) include the drilling fluid tanks, the drilling fluid pumps (e.g., rig mixing pumps), the derrick or mast, the draw works, the rotary table or top drive, the drill string, the power generation equipment and auxiliary equipment.

The wellbore (120) includes a bored hole (i.e., borehole) that extends from the surface (108) into a target zone of the hydrocarbon-bearing formation (104), such as the reservoir (102). An upper end of the wellbore (120), terminating at or near the surface (108), may be referred to as the "up-hole" end of the wellbore (120), and a lower end of the wellbore, terminating in the hydrocarbon-bearing formation (104), may be referred to as the "downhole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the hydrocarbon-bearing formation (104) or the reservoir (102) during injection operations, or the communication of monitoring devices (e.g., logging tools) lowered into the hydrocarbon-bearing formation (104) or the reservoir (102) during monitoring operations (e.g., during in situ logging operations).

In some embodiments, during operation of the well system (106), the well control system (126) collects and records well data (140) for the well system (106). During drilling operation of the well (106), the well data (140) may include mud properties, flow rates, drill volume and penetration rates, formation characteristics, etc. The well data (140) may also include sensor data of the taggant detector (201) depicted in FIG. 2 below. In some embodiments, the well data (140) are recorded in real-time, and are available for review or use within seconds, minutes or hours of the condition being sensed (e.g., the measurements are available within 1 hour of the condition being sensed). In such an embodiment, the well data (140) may be referred to as "real-time" well data (140). Real-time well data (140) may enable an operator of the well (106) to assess a relatively current state of the well system (106), and make real-time decisions regarding a development of the well system (106) and the reservoir (102), such as on-demand adjustments in drilling fluid and regulation of production flow from the well.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more production valves (132) that are operable to control the flow of production (134). For example, a production valve (132) may be fully opened to enable the unrestricted flow of production (121) from the wellbore (120), the production valve (132) may be partially opened to partially restrict (or "throttle") the flow of production (121) from the wellbore (120), and production valve (132) may be fully closed to fully restrict (or "block") the flow of production (121) from the wellbore (120), and through the well surface system (124).

In some embodiments, the wellhead (130) includes a choke assembly. For example, the choke assembly may include hardware with functionality for opening and closing the fluid flow through pipes in the well system (106). Likewise, the choke assembly may include a pipe manifold that may lower the pressure of fluid traversing the wellhead. As such, the choke assembly may include a set of high pressure valves and at least two chokes. These chokes may be fixed or adjustable or a mix of both. Redundancy may be provided so that if one choke has to be taken out of service, the flow can be directed through another choke. In some embodiments, pressure valves and chokes are communicatively coupled to the well control system (126). Accordingly, a well control system (126) may obtain wellhead data regarding the choke assembly as well as transmit one or more commands to components within the choke assembly in order to adjust one or more choke assembly parameters.

Keeping with FIG. 1, in some embodiments, the well surface system (124) includes a surface sensing system (134). The surface sensing system (134) may include sensors for sensing characteristics of substances, including production (121), passing through or otherwise located in the well surface system (124). The characteristics may include, for example, pressure, temperature and flow rate of production (121) flowing through the wellhead (130), or other conduits of the well surface system (124), after exiting the wellbore (120). The surface sensing system (134) may also include sensors for sensing characteristics of the rig (101), such as bit depth, hole depth, drilling fluid flow, hook load, rotary speed, etc. Further, the taggant detector (201) depicted in FIG. 2 below may be included as part of the surface sensing system (134).

In some embodiments, the well system (106) is provide with an analysis engine (160). For example, the taggant analysis and control engine (202) depicted in FIG. 2 below may be part of the analysis engine (160) that includes hardware and/or software with functionality for analyzing the drilling fluid and taggant impregnated rock cuttings to determine the depth of the drill bit where the rocking cuttings are generated. The depth of the drill bit where the rocking cuttings are generated is referred to as the cuttings' depth of origin. Accurate determination of the cuttings' depth of origin for mud logging improves the quality in geosteering, well placement, and petrophysical analysis through real time formation evaluation. The analysis engine (160) may also include a reservoir simulator that includes hardware and/or software with functionality for generating one or more reservoir models regarding the hydrocarbon-bearing formation (104) and/or performing one or more reservoir simulations. The reservoir model and reservoir simulation may be advantageously generated/performed based on the aforementioned improved well placement and petrophysical analysis. Accordingly, the reservoir development planning and/or production operation are improved based on the result generated by the analysis engine (160).

While the analysis engine (160) is shown at a well site, in some embodiments, the analysis engine (160) is located away from well site, such as in the Cloud over the Internet. In some embodiments, the analysis engine (160) may include a computer system that is similar to the computer system (500) described below with regard to FIGS. 5A and 5B and the accompanying description.

Figure 2:
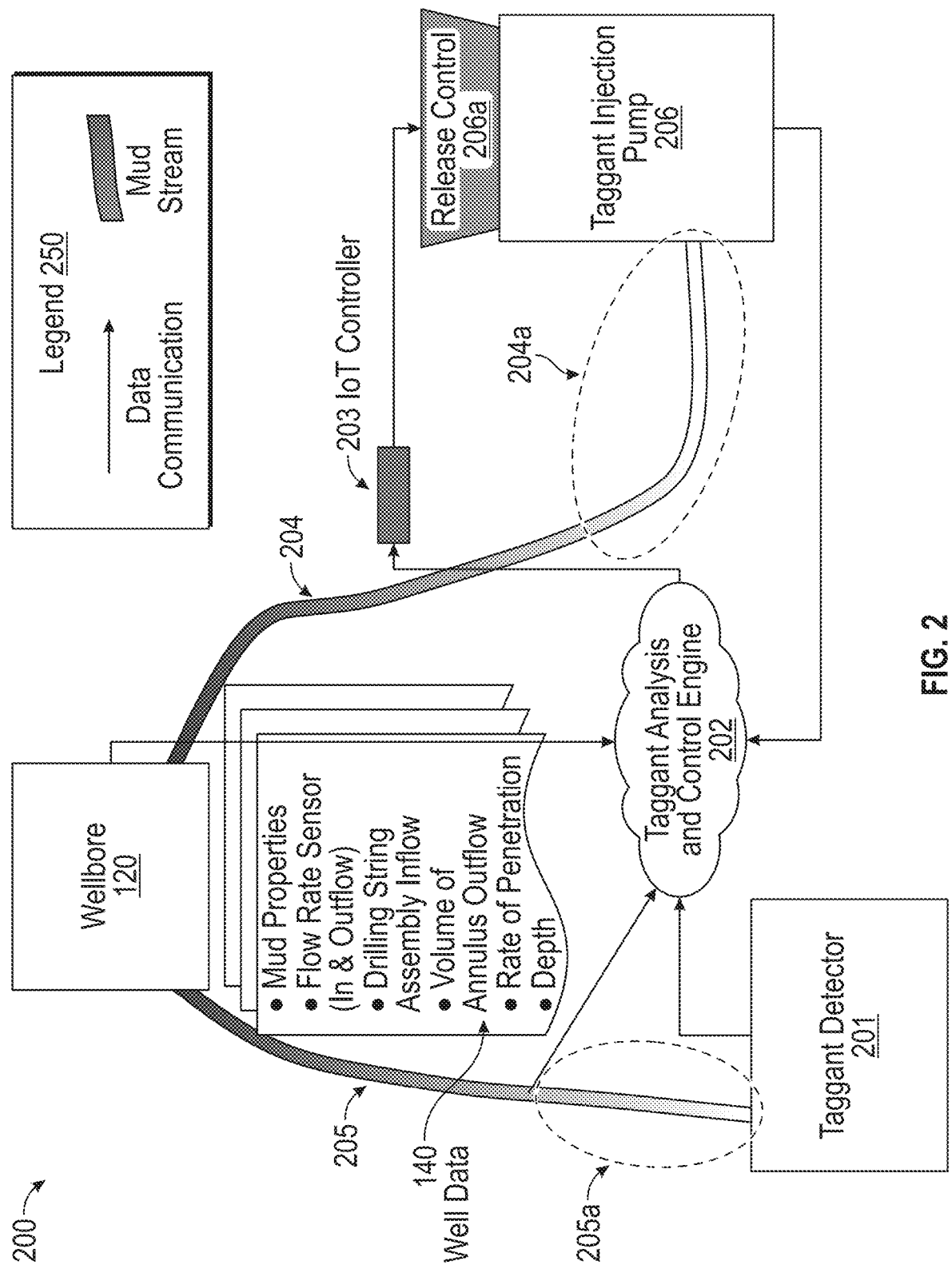

Turning to FIG. 2, FIG. 2 illustrates an example system in accordance with one or more embodiments of the invention.

In one or more embodiments, one or more of the modules and/or elements shown in FIG. 2 may be omitted, repeated, and/or substituted. Accordingly, embodiments of the invention should not be considered limited to the specific arrangements of modules and/or elements shown in FIG. 2.

Lack of accurate determination of the cuttings' depth of origin limits the efficacy of conventional mud logging due to depth uncertainty of several feet (ft), especially in deviated and horizontal wells where cuttings' flows may be delayed due to gravitational debris accumulation, and problematic hydraulics and hole cleaning. Accurate determination of the cuttings' depth of origin depends on wellbore mud hydraulics, hole cleaning, accurate knowledge of the return-trip delay time up in the annulus, discrimination of caving and potentially delayed cuttings returning to the surface, etc. Even in normal flow conditions, the depth uncertainties can reach more than 20 ft if the cuttings' upward trip lasts more than 30 minutes. Any inaccuracy in labeling of the collected cuttings further increases these errors.

FIG. 2 shows a system (200) for automatically and accurately determining, while drilling, the depth of origin of rock cuttings carried to the surface in the mud stream. In one or more embodiments of the invention, the system (200) is part of the well system (106) depicted in FIG. 1 above. As shown in FIG. 2, the system (200) includes a taggant detector (201), a taggant analysis and control engine (202), an IoT controller (203), and a taggant injection pump (204) that collectively detect, analyze, and control the taggant release into the mud stream (204, 205) of the wellbore (120). For example, the taggant detector (201), the IoT controller (203), and the taggant injection pump (204) may be part of the well control system (126) depicted in FIG. 1 above. The taggant analysis and control engine (202) may be part of the analysis engine (160) depicted in FIG. 1 above. As shown in FIG. 2 based on the legend (250), the arrows represent data communication among various components of the system (200), and the shaded curves represent the mud streams. In particular, the mud stream (204) travels downhole and the mud stream (205) returns to the surface. The lighter shaded portion (204a) of the mud stream (204) represents the taggant released into the mud stream traveling downhole. The lighter shaded portion (205a) of the mud stream (205) represents the taggant impregnated onto the rock cuttings carried by the mud stream returning to the surface.

In one or more embodiments of the invention, the taggant detector (201) detects and analyzes the taggant impregnated on the rock cuttings as the rock are carried to the surface in the mud stream. The detection data, in addition to mud properties, flow rates, drill volume and penetration rates, formation nature, and well specifications (depth, diameter, geometries, etc.) are then transferred to the taggant analysis and control engine (202).

In one or more embodiments of the invention, the taggant analysis and control engine (202) analyzes the detection data and other information from the taggant detector (201), in real-time, to generate injection profiles. The injection profiles are sent to and used by the IoT controller (203) to adapt the injection parameters of the taggant injection pump (204) for achieving an intelligent controlled release of the taggant. In one or more embodiments, the taggant analysis and control engine (202) generates injection profiles using artificial intelligence and machine learning algorithms. For example, the taggant analysis and control engine (202) may be trained by a sequence of injection patterns, respective nanotag recordings, flow speeds and depth. The taggant analysis and control engine (202) optimizes a quantity and an injection speed of the injected taggant to achieve defined conditions. For example, if a recorded concentration of a specific taggant is low, making it indistinguishable from the other taggant, then the IoT controller (203) may increase the concentration of this taggant.

In one or more embodiments of the invention, the IoT controller (203) controls the taggant injection pump (204) to release the taggant into the mud stream to ensure that different batches of taggant impregnated rock cuttings generated during various stages of the drilling operations are distinguishable. As noted above, the IoT controller (203) controls the taggant injection pump (204) by adapting the injection parameters based on the injection profiles received from the taggant analysis and control engine (202).

In one or more embodiments of the invention, the taggant injection pump (204) includes multiple injector valves connected to a number of different container chambers (for holding the taggant) with different sizes that are selectable based on the injection profiles. The IoT controller (203) interfaces with the taggant injection pump (204) to control both the degree of the shutting and opening of the injector valves for the respective chambers, as well as the pressure at the injector valves. The taggant injection pump (204) is a metering pump that allows exact amount of taggant to be injected into the drilling fluid. While the taggant injection pump (204) automatically adjusts the release valves based on the injection parameters from the IoT controller (203), the taggant injection pump (204) also allows for manual adjustment of the release valves.

In one or more embodiments of the invention, the taggant includes polymeric nanoparticles dispersed in an aqueous fluid, which is added in small doses directly into drilling fluids. The polymeric nanoparticles are one type of taggant referred to as "NanoTags." The term "NanoTags" may also refer to other types of taggant such as metal microdots with etched identification codes. Due to the small size and chemical nature of the NanoTags or polymeric nanoparticles, the taggant permanently attaches to rock cuttings as the rock cuttings are cut at the drill bit face. The taggant impregnates the rock cuttings by remaining on and embedded inside the pores of the rock cuttings as the rock cuttings return to the surface in the mud stream. Based on the encoded identification code of the NanoTags or polymeric nanoparticles, the depth determination of the taggant impregnated rock cuttings has a depth uncertainty within 1 ft and is not affected even if different batches of rock cuttings are shifted or mixed up during transport of storage prior to being analyzed. Accordingly, the system (200) improves the quality of petrophysical analysis of the rock cuttings based on the improved depth accuracy of mud logging.

Figure 3A:
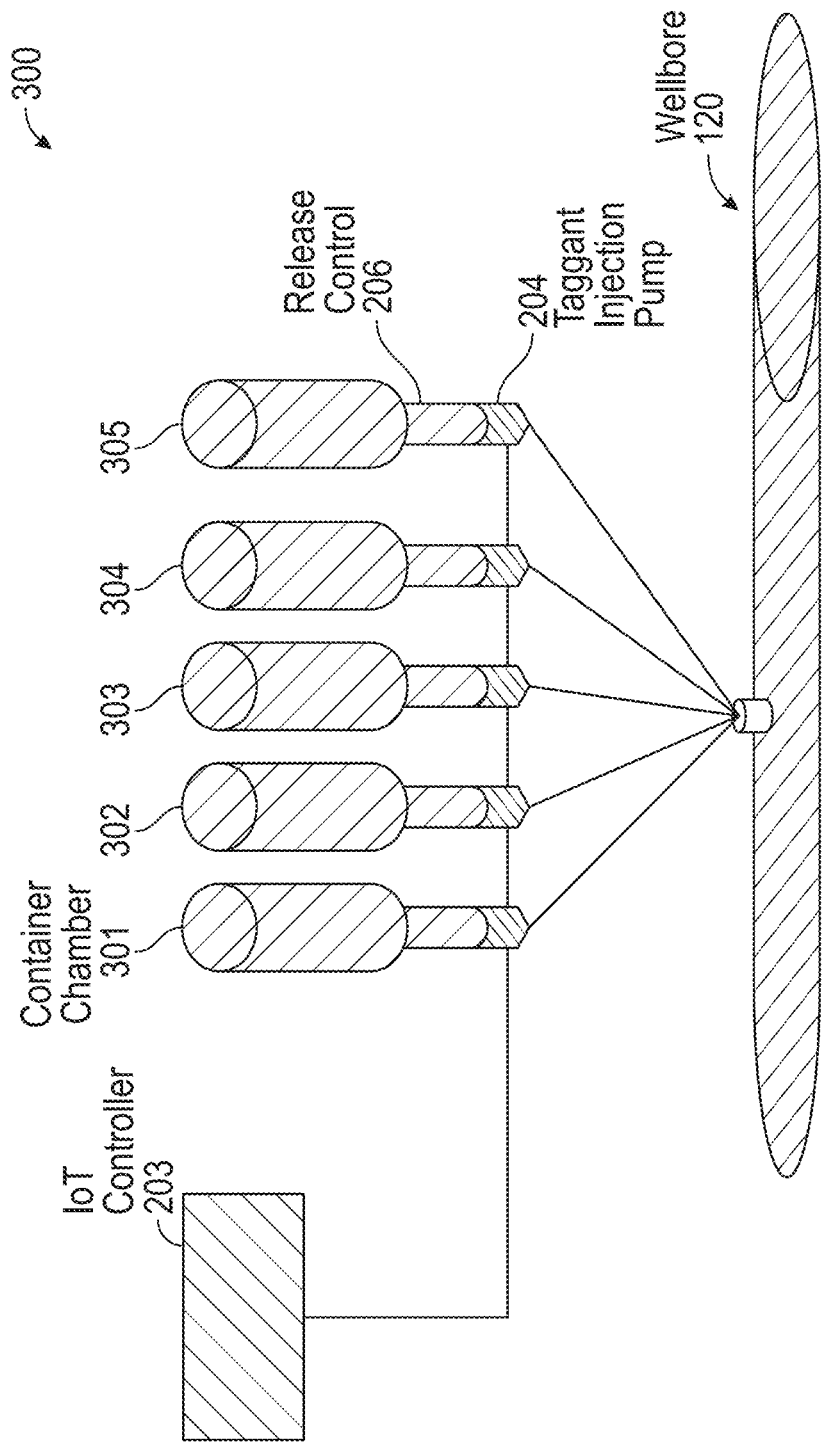
FIGS. 3A, 3B, 3C and 3D show examples of system in accordance with one or more embodiments.

Turning to FIG. 3A, FIG. 3A illustrates an example system in accordance with one or more embodiments of the invention. In one or more embodiments, one or more of the modules and/or elements shown in FIG. 3A may be omitted, repeated, and/or substituted. Accordingly, embodiments of the invention should not be considered limited to the specific arrangements of modules and/or elements shown in FIG. 2.

FIG. 3A shows a system (300) for controlling automatic and accurate injection of taggant in the mud stream. In one or more embodiments of the invention, the system (300) is part of the well system (106) depicted in FIG. 1 above. As shown in FIG. 3A, the system (300) includes the IoT controller (203), the taggant injection pump (204), the containers (301-305) and release control (206), and the wellbore (120). For example, the IoT controller (203), and the taggant injection pump (204) may be part of the well control system (126) depicted in FIG. 1 above.

As noted above, the IoT controller (203) controls the taggant injection pump (204) to release the taggant into the mud stream. The IoT Controller (203) in one or more embodiments may comprise a smart controller and a CPU, that processes recommendations of the taggant analysis and control engine (202), and then returns control instructions to the taggant injection pump (204). For example, the control instructions provided by the IoT Controller (203) may be a volume of taggant injected, a flow rate and a spacing between different taggant injections. The control instructions may be submitted via network cables that electronically open the release control (206) to adapt the flow rate and volume. Additionally or alternatively, the control instructions may be submitted via wireless connectivity. For example the wireless connectivity may be achieved with at least: LTE/5G, narrowband, e.g., NB-IoT, LoraWAN, ISA-100, etc.

As mentioned above, the taggant injection pump (204) includes the release valves (206) connected to the container chambers (301, 302, 303, 304 and 305). Each container chamber (301, 302, 303, 304 and 305) may contain a different type of taggant. Multiple taggant types may be necessary to more accurately determine the properties of the well. Each taggant type, when released to the fluid flow, leaves a trace on rock cuttings. During the analysis, the data regarding how each taggant type was released, together with the data regarding the rock cuttings on which that particular taggant type was detected on, may provide the information regarding well properties. The types of taggants may differ by the sizes that are selectable based on the injection profiles. Utilizing multiple taggants of various types enables differentiating rock cuttings between various depths. As each taggant type may have different properties, it may give an insight in different parts and properties of the well. Hence, the precision of determining multiple rock depth layers is increased by increasing the number of chambers containing different taggants.

Figure 3B:
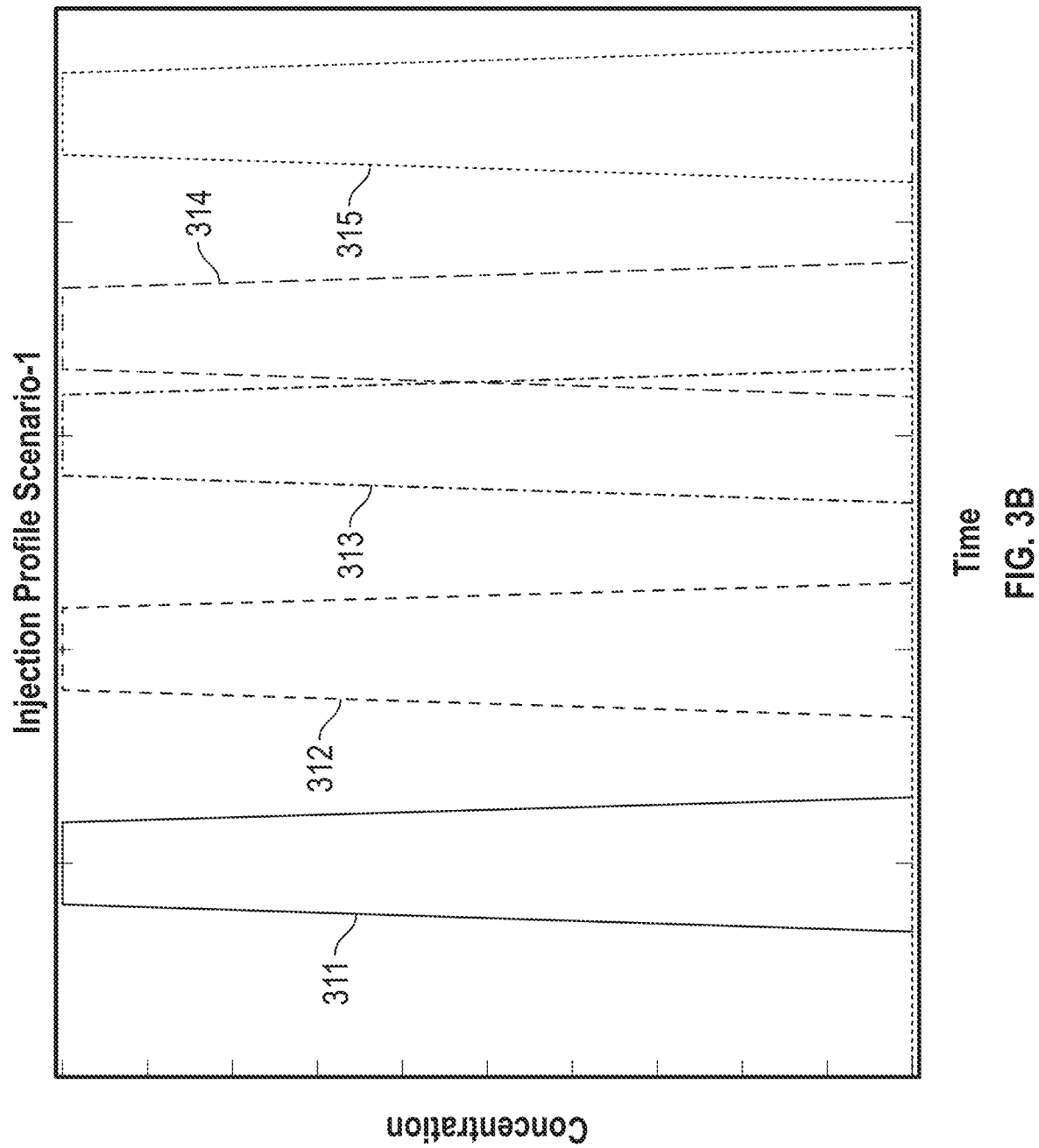

FIG. 3B shows sample injection profiles containing five different taggants. Each taggant type is stored in a separate container chamber. In this example, different taggants types are stored in container chambers (301, 302, 303, 304 and 305), depicted in FIG. 3A above. Furthermore, graphs of the sample injection profiles (311, 312, 313, 314 and 315) respectively correspond to different taggant types stored in container chambers (301, 302, 303, 304 and 305), depicted in FIG. 3A above. The sample injection profiles, shown in FIG. 3B, represent an idealistic injection scenario. The term idealistic may be used because, for each injection, the optimal concentration of the taggant type was utilized. The graph of the injection profile (311) corresponds to a first batch of taggant, injected into the mud for a certain period during the drilling operation. As shown in FIG. 3B, initially, the taggant type of the injection profile (311) is released gradually, from the container chamber (301), with a linear increase of the concentration. The injection of the first batch of taggant continues until the adequate percentage of impregnated rock cuttings are detected and analyzed at the surface. In this example injection profile (311), the concentration of taggant, represented in the graph as the vertical axis, was correctly estimated, as the rock cuttings were detected after the symmetrical increase of the concentration to its peak and decrease of the concentration to zero. After the detection of the taggant, the depth of the drill bit is recorded as the rock cuttings' depth of origin. The first analysis sample is uniquely identified by the identification code encoded on each nanoparticle in the first batch of taggant. The rock properties of the first analysis sample are recorded with respect to the rock cutting's depth of origin, i.e., the depth of the drill bit at the time of detecting adequate percentage of impregnated rock cuttings with the first batch of taggant.

Subsequently, the second batch of taggant, represented in the graph as (312), stored in the container chamber (302) are injected into the drilling fluid to travel down the formation. For example, injection of the second batch of taggant may start upon detecting the adequate percentage of the impregnated rock cuttings with the first batch of taggant. The taggant is released gradually, from the container chamber (302), with a linear increase of the concentration. The injection of the second batch of taggant continues until the adequate percentage of the impregnated rock cuttings are detected and analyzed at the surface. In this example injection profile (312), the concentration of taggant, represented in the graph as the vertical axis, was also correctly estimated, as the rock cuttings were detected after the symmetrical increase of the concentration to its peak and decrease of the concentration to zero. After detecting the taggant, the depth of the drill bit is recorded as the rock cuttings' depth of origin. The second analysis sample is uniquely identified by the identification code encoded on each nanoparticle in the second batch of taggant. The rock properties of the second analysis sample are recorded with respect to the rock cutting's depth of origin, i.e., the depth of the drill bit at the time of detecting adequate percentage of impregnated rock cuttings with the second batch of taggant. The same procedure, with similar results, is done with the injection profiles represented in graph as (313, 314 and 315) stored in container chambers (303, 304 and 305), depicted in FIG. 3A above.

Figure 3C:
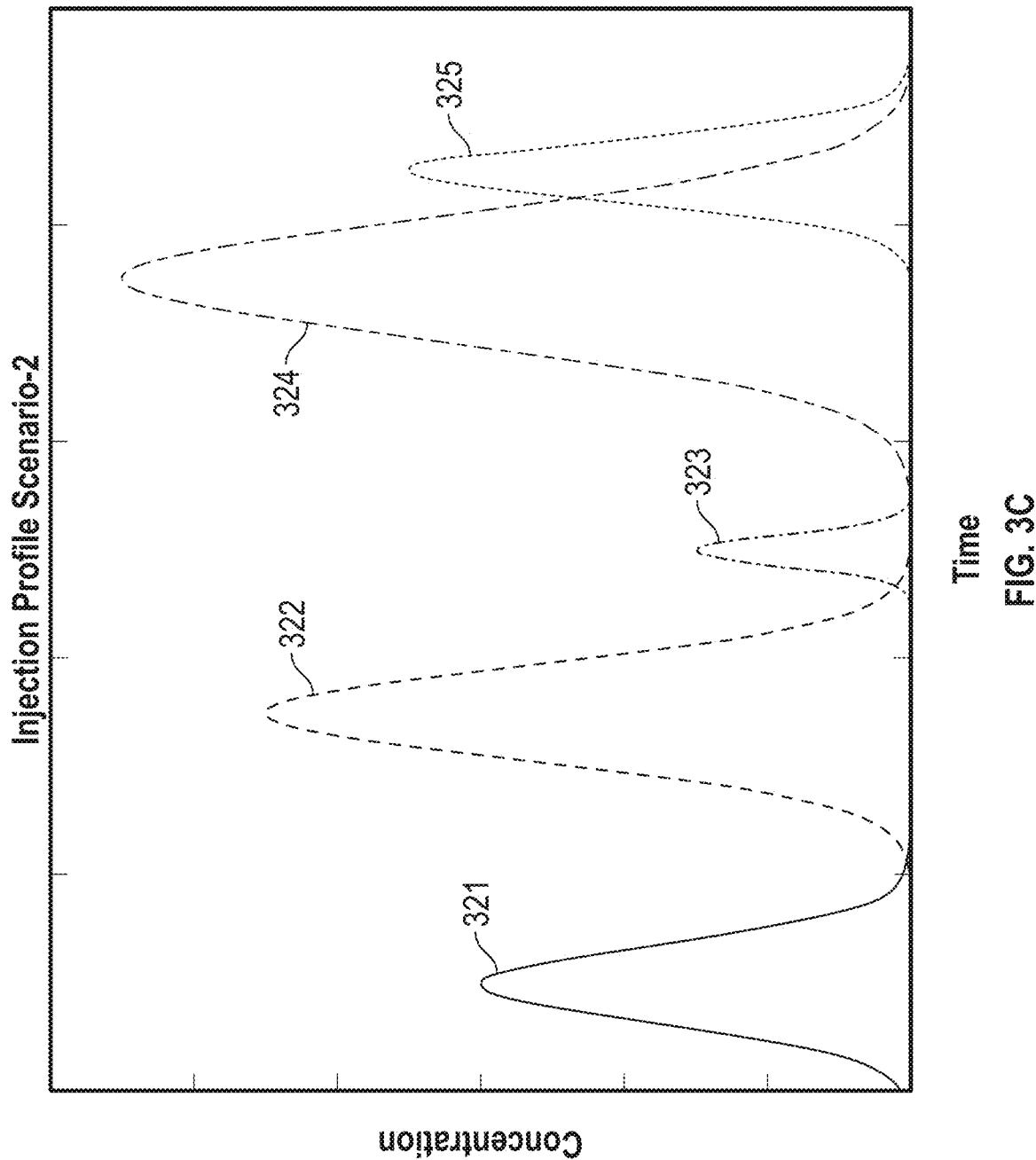

FIG. 3C, similarly to FIG. 3B, shows a sample injection profile containing five different taggants. Each taggant type is stored in a separate container chamber. In this example, different taggants types are stored in container chambers (301, 302, 303, 304 and 305), depicted in FIG. 3A above. Furthermore, graphs of the sample injection profiles (321, 322, 323, 324 and 325) respectively correspond to different taggant types stored in container chambers (301, 302, 303, 304 and 305), depicted in FIG. 3A above. This sample injection profile also represents an idealistic injection scenario. As shown in FIG. 3C, initially, the taggant, represented in the graph as (321), is released gradually, from the container chamber (301), forming a sinusoidal graph. The injection of the first batch of taggant, represented in the graph as (321), continues until the adequate percentage of impregnated rock cuttings are detected and analyzed at the surface. In this example injection profile (321), the concentration of taggant, represented in the graph as the vertical axis, was correctly estimated, as the rock cuttings were detected after the symmetrical increase of the concentration to its peak and decrease of the concentration to zero. After detecting the taggant, the depth of the drill bit is recorded as the rock cuttings' depth of origin. The first analysis sample is uniquely identified by the identification code encoded on each nanoparticle in the first batch of taggant. The rock properties of the first analysis sample are recorded with respect to the rock cutting's depth of origin, i.e., the depth of the drill bit at the time of detecting adequate percentage of impregnated rock cuttings with the first batch of taggant.

Subsequently, the second batch of taggant, represented in the graph as (322), stored in the container chamber (302) are injected into the drilling fluid to travel down the formation. For example, injection of the second batch of taggant may start upon detecting the adequate percentage of the impregnated rock cuttings with the first batch of taggant. The taggant, represented in the graph as (322), is released gradually, from the container chamber (302), forming the sinusoidal graph. The injection of the second batch of taggant continues until impregnated rock cuttings are detected and analyzed at the surface. In this example injection profile (322), the concentration of taggant, represented in the graph as the vertical axis, was also correctly estimated, as the rock cuttings were detected after the symmetrical increase of the concentration to its peak and decrease of the concentration to zero. After detecting the taggant, the depth of the drill bit is recorded as the rock cuttings' depth of origin. The second analysis sample is uniquely identified by the identification code encoded on each nanoparticle in the second batch of taggant. The rock properties of the second analysis sample are recorded with respect to the rock cutting's depth of origin, i.e., the depth of the drill bit at the time of detecting adequate percentage of impregnated rock cuttings with the second batch of taggant. The same procedure, with similar results, is done with the injection profiles, represented in graph as (323, 324 and 325), stored in container chambers (303, 304 and 305), depicted in FIG. 3A above.

Figure 3D:
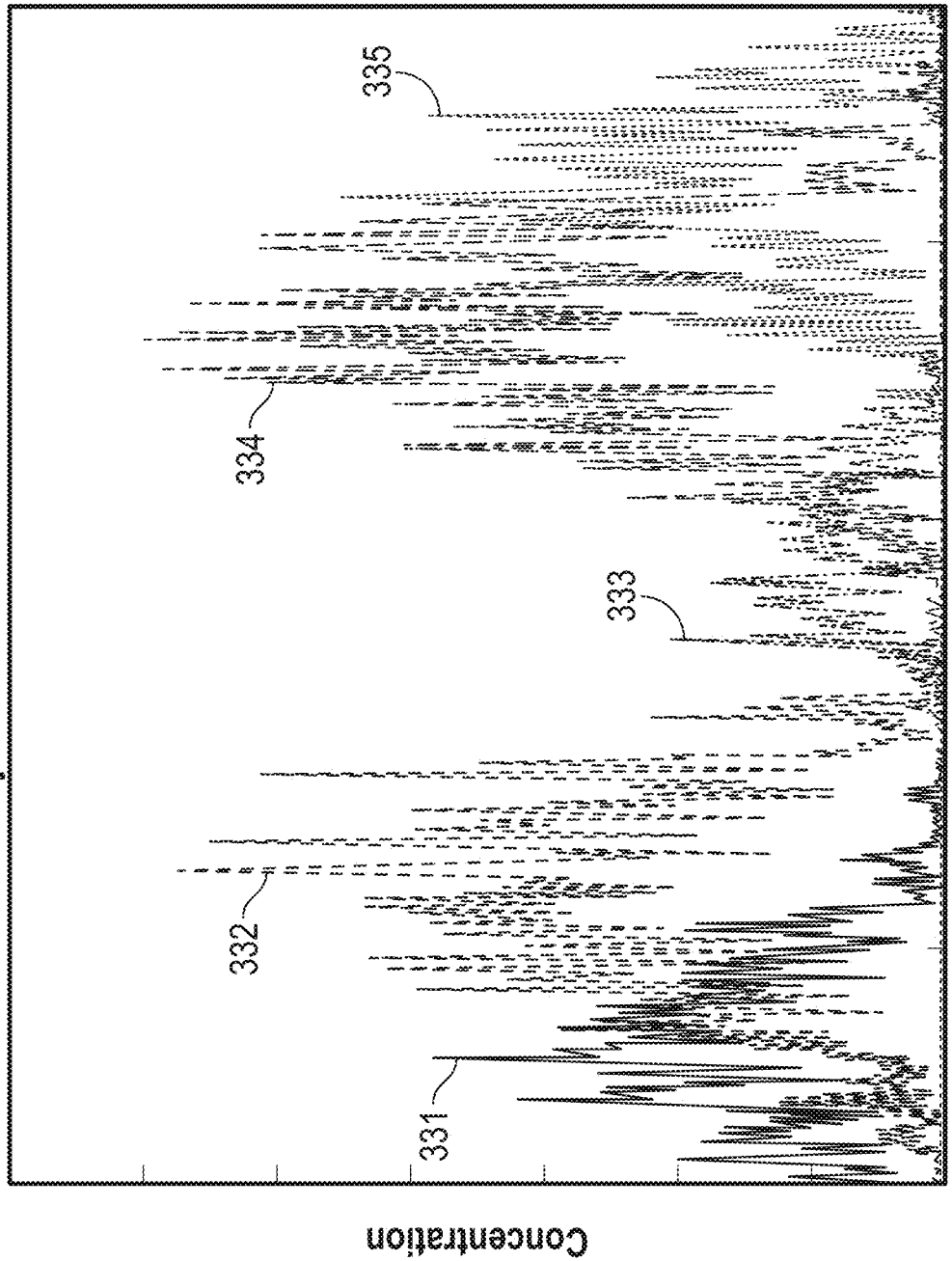

FIG. 3D shows a sample injection profile containing five different taggants. Each taggant type is stored in a separate container chamber. In this example, different taggants types are stored in container chambers (301, 302, 303, 304 and 305), depicted in FIG. 3A above. Furthermore, graphs of the sample injection profiles (331, 332, 333, 334 and 335) respectively correspond to different taggant types stored in container chambers (301, 302, 303, 304 and 305), depicted in FIG. 3A above. This sample injection profile represents a more extreme scenario of concentration adaptions. In this case, the injection profile is repeatedly adjusted according to the analysis of real-time data, received from the taggant detector. Based on the feedback from the taggant analysis and control engine, the IoT controller (203) increases or decreases the concentration of each taggant type, to achieve the optimal concentration. As shown in FIG. 3D, initially, the taggant, represented in the graph as (331), is released from the container chamber (301). When the taggant is released, the injection pump (204) starts receiving control signals from the IoT controller (203) regarding the injection process, wherein the control signals are based on the injection profile. As the entire process is analyzed in the real-time, the IoT controller (203) receives a frequent feedback. Based on the feedback, the IoT controller (203) sends the control signals to the injection pump (204), in the attempt to reach the injection of the optimal concentration. In this example, the injection profile (311) incorrectly estimates the concentration of the taggant, represented in the graph as the vertical axis. However, due to the feedback form the real-time analysis, the IoT controller (203) is able to adjust the injected concentration of the taggant, to achieve the optimal result. Hence, the fluctuations may be noticed in FIG. 3D. The injection of the first batch of taggant continues until the adequate percentage of impregnated rock cuttings are detected and analyzed at the surface. After detecting the taggant, represented in the graph as (331), the depth of the drill bit is recorded as the rock cuttings' depth of origin. The first analysis sample is uniquely identified by the identification code encoded on each nanoparticle in the first batch of taggant. The rock properties of the first analysis sample are recorded with respect to the rock cutting's depth of origin, i.e., the depth of the drill bit at the time of detecting adequate percentage of impregnated rock cuttings with the first batch of taggant.

Subsequently, the second batch of taggant, represented in the graph as (332), stored in the container chamber (302) are injected into the drilling fluid to travel down the formation. For example, injection of the second batch of taggant may start upon detecting the adequate percentage of the impregnated rock cuttings with the first batch of taggant. As shown in FIG. 3D, the injection of taggant starts when the taggant detector estimates that the adequate percentage of the impregnated rock cutting are received. The system (300) reacts by decreasing the concentration of the taggant, represented in the graph as (331) and by starting to inject the taggant, represented in the graph as (332). However, due to the unoptimized injection profile, the injection pump starts injecting the taggant, represented in the graph as (332), early. Hence, both, taggant, represented in the graph as (331), and taggant, represented in the graph as (332), are simultaneously injected for a period of time. The injection of the second batch of taggant, represented in the graph as (322), continues until impregnated rock cuttings are detected and analyzed at the surface. After detecting the taggant, the depth of the drill bit is recorded as the rock cuttings' depth of origin. The second analysis sample is uniquely identified by the identification code encoded on each nanoparticle in the second batch of taggant. The rock properties of the second analysis sample are recorded with respect to the rock cutting's depth of origin, i.e., the depth of the drill bit at the time of detecting adequate percentage of impregnated rock cuttings with the second batch of taggant. The same procedure is done with the injection profiles represented in graph as (333, 334 and 335) stored in container chambers (303, 304 and 305), depicted in FIG. 3A above, respectively.

In one or more embodiments the IoT Controller (203) may open only one release control (204) as a safety feature. For example, the safety feature may protect the system (300) in case multiple release controls is open manually. Opening and switching between different release controls (204) may require at least a fraction of a second.

Figure 4:
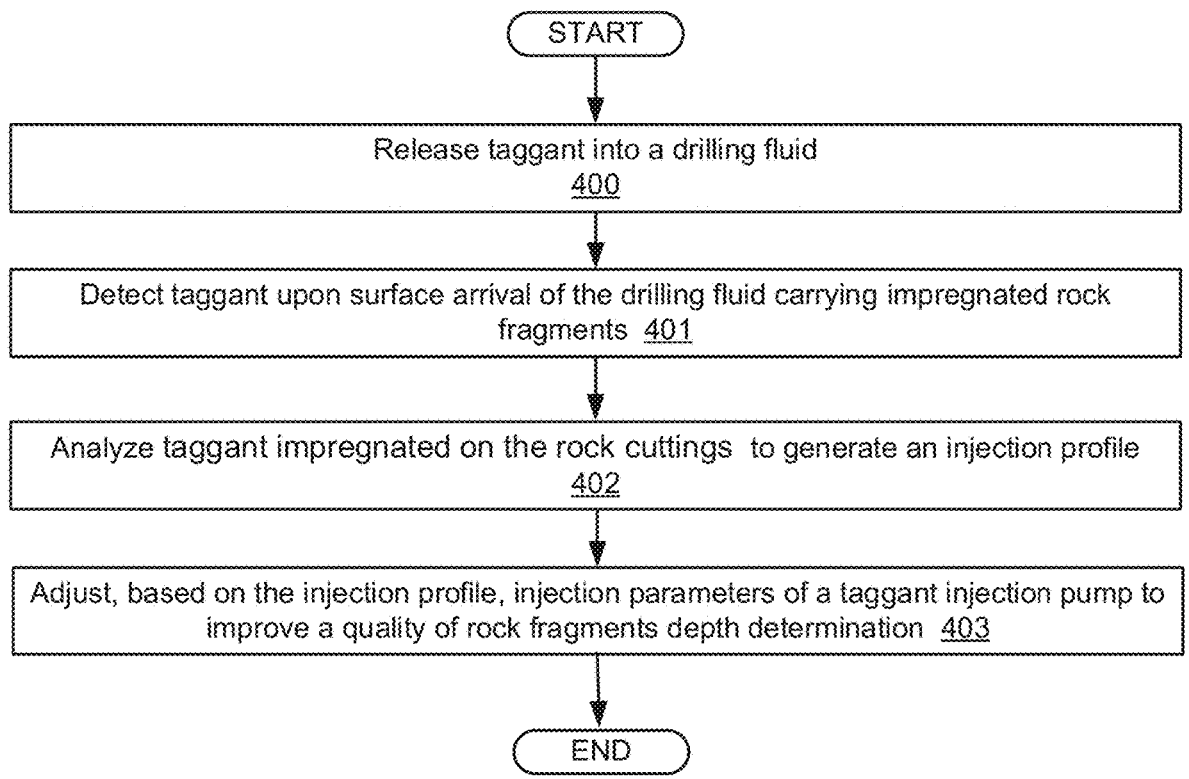
FIG. 4 shows a flowchart in accordance with one or more embodiments.

Turning to FIG. 4, FIG. 4 shows a method flowchart in accordance with one or more embodiments. One or more blocks in FIG. 4 may be performed using one or more components as described in FIGS. 1, 2 and 3. While the various blocks in FIG. 4 are presented and described sequentially, one of ordinary skill in the art will appreciate that some or all of the blocks may be executed in different orders, may be combined or omitted, and some or all of the blocks may be executed in parallel and/or iteratively. Furthermore, the blocks may be performed actively or passively.

Initially in Block 400, using a taggant injection pump, during the drilling operation, a taggant is injected into a drilling fluid. The taggant is injected according to an initial injection profile. Generally, the injection profile specifies various injection parameters such as the quantity of taggant, the injection pressure of the taggant injection pump, the degree of shutting and opening of individual injector valves, the injection time window, the time separation from injecting the previous batch of taggant (i.e., injection time lag), etc. The taggant is transported downhole by the drilling fluid to impregnate rock cuttings as the cuttings are produced by a drill bit. In one or more embodiments of the invention, the taggant includes polymeric nanoparticles where each nanoparticle is encoded with an identification code unique to the taggant.

In Block 401, using a taggant detector at a surface location, a taggant is detected upon surface arrival of the rock cuttings. The taggant detector detects the taggant based on the optical, chemical, electrical, or mechanical characteristic of the nanoparticles in the taggant. The taggant is transported up-hole by the drilling fluid subsequent to impregnate the rock cuttings downhole.

In Block 402, using a taggant analysis and control engine, an overlap of the time-dependent signals is analyzed to generate a new injection profile. In one or more embodiments of the invention, the analysis includes one or more of determining respective signal peaks and half-widths of the first time-dependent signal and the second time-dependent signal, determining a time gap between the two signal peaks and a signal floor within the time gap, and determining other timing waveform statistics. The overlap is defined as a measure based on the respective signal peaks and half-widths, the time gap, the signal floor, and other timing waveform statistics. For example, the overlap may be defined as the ratio of the sum of the half-widths over the time gap. The overlap may be further qualified or modified by the ratio of one or both signal peak magnitude over the signal floor. The first time-dependent signal and the second time-dependent signal are determined to be distinguishable from each other, i.e., with minimum overlap, if each of the respective signal peaks exists and has a magnitude exceeding the signal floor by a predetermined threshold, such as 30% of the signal peak magnitude. The first time-dependent signal and the second time-dependent signal are determined to be not sufficiently distinguishable from each other if each of the respective signal peaks does not separately exist or if the overlap of the two time dependent signals exceeds a predetermined threshold.

In one or more embodiments, a new injection profile is generated using a machine learning model generated by the taggant analysis and control engine. The machine learning model is trained using a training data set that includes a large number of time dependent signals with corresponding injection profiles, as well as associated well site parameters for the drilling operation, such as mud properties, drill bit depth, rate of penetration, formation characteristics, etc. For example, the training data set may include the first injection profile and the second injection profile that yield the first time-dependent signal and the second time-dependent signal as distinguishable from each other and are marked as adequate injection profiles. In another example, the training data set may include the first injection profile and the second injection profile that yield the first time-dependent signal and the second time-dependent signal as not sufficiently distinguishable from each other and are marked as inadequate injection profiles. Accordingly, the third injection profile is generated using the trained machine learning model taking the well site parameters as inputs. In other words, the third injection profile is dependent on the mud properties, drill bit depth, rate of penetration, formation characteristics, etc. at the time of injecting the third batch of taggant. Specifically, such dependency is captured in and modeled by the machine learning model. As a result, a taggant injected according to the third injection profile yields a distinguishable third time dependent signal under the well site condition at the time of injecting the taggant.

In Block 403, based on the new injection profile, the injection parameters of the taggant injection pump are adjusted to improve a quality of the rock cutting depth determination for mud logging. In one or more embodiments, the new injection profile is sent from the taggant analysis and control engine to an IoT controller. Accordingly, the IoT controller adjusts the injection parameters of the taggant injection pump based on the injection profile. In one or more embodiments, the taggant analysis and control engine resides on a Cloud server and the IoT controller resides in proximity to the taggant injection pump at the well site. In particular, the taggant analysis and control engine communicates with the IoT controller via a network connection (e.g., Internet) to send the injection profiles.

Figure 5A:
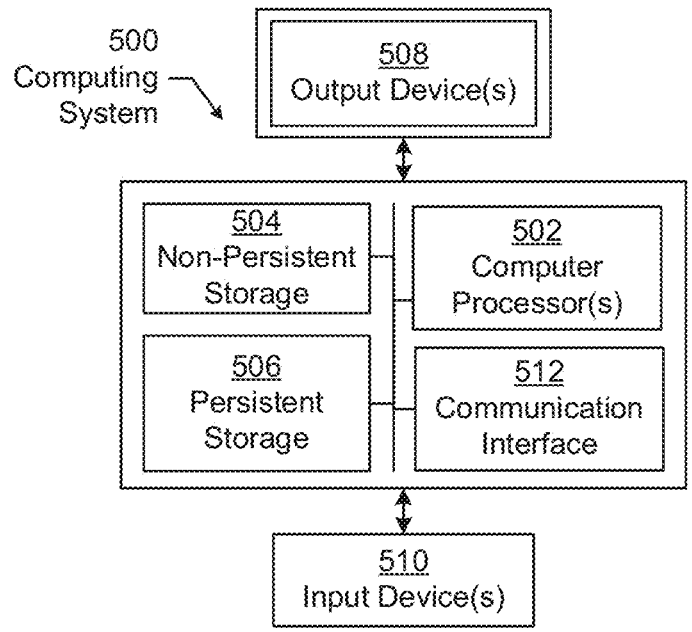
FIGS. 5A and 5B show a computing system in accordance with one or more embodiments.

Embodiments may be implemented on a computing system. Any combination of mobile, desktop, server, router, switch, embedded device, or other types of hardware may be used. For example, as shown in FIG. 5A, the computing system (500) may include one or more computer processors (502), non-persistent storage (504) (e.g., volatile memory, such as random access memory (RAM), cache memory), persistent storage (506) (e.g., a hard disk, an optical drive such as a compact disk (CD) drive or digital versatile disk (DVD) drive, a flash memory, etc.), a communication interface (512) (e.g., Bluetooth interface, infrared interface, network interface, optical interface, etc.), and numerous other elements and functionalities.

The computer processor(s) (502) may be an integrated circuit for processing instructions. For example, the computer processor(s) may be one or more cores or micro-cores of a processor. The computing system (500) may also include one or more input devices (510), such as a touchscreen, keyboard, mouse, microphone, touchpad, electronic pen, or any other type of input device.

The communication interface (512) may include an integrated circuit for connecting the computing system (500) to a network (not shown) (e.g., a local area network (LAN), a wide area network (WAN) such as the Internet, mobile network, or any other type of network) and/or to another device, such as another computing device.

Further, the computing system (500) may include one or more output devices (508), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (502), non-persistent storage (504), and persistent storage (506). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 5B:
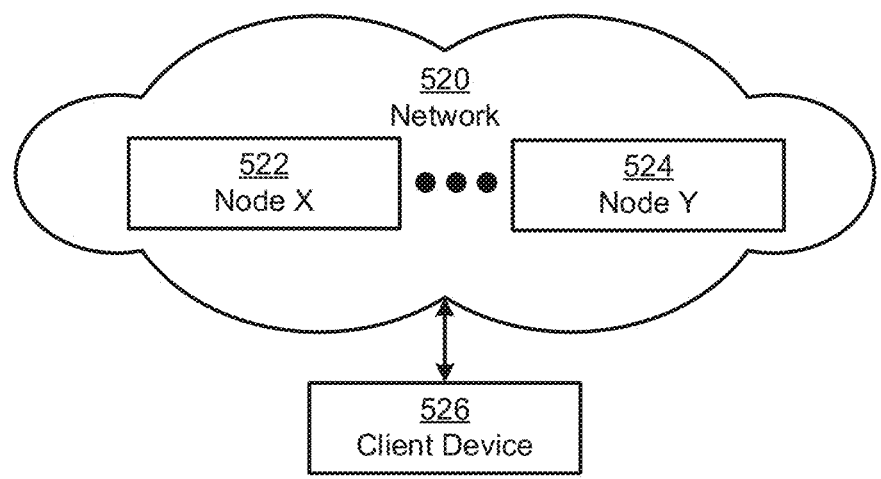

The computing system (500) in FIG. 5A may be connected to or be a part of a network. For example, as shown in FIG. 5B, the network (520) may include multiple nodes (e.g., node X (522), node Y (524)). Each node may correspond to a computing system, such as the computing system shown in FIG. 5A, or a group of nodes combined may correspond to the computing system shown in FIG. 5A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (500) may be located at a remote location and connected to the other elements over a network.

Although not shown in FIG. 5B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (522), node Y (524)) in the network (520) may be configured to provide services for a client device (526). For example, the nodes may be part of a cloud computing system. The nodes may include functionality to receive requests from the client device (526) and transmit responses to the client device (526). The client device (526) may be a computing system, such as the computing system shown in FIG. 5A. Further, the client device (526) may include and/or perform all or a portion of one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A system for drilling a wellbore, comprising:
    a drill string disposed in the wellbore, the drill string having a central aperture and defining an annulus between the drill string and side walls of the wellbore;
    a taggant injection pump in fluid communication with a circulation path for a drilling fluid and configured to selectively inject taggants into the drilling fluid;
    a processor arranged to control the taggant injection pump;
    a taggant detector in fluid communication with a return part of the circulation path, the taggant detector producing information relating to the taggants detected in the drilling fluid; and
    a taggant analysis and control engine that receives the information from the taggant detector, analyzes the information in real time, and provides instructions to the processor to improve a quality of a rock cutting depth determination,
    wherein mud logging is performed based on the improved quality of the rock cutting depth determination, and wherein the taggant analysis and control engine uses a machine learning model to forecast, in real time, quantities and concentrations of the taggants detected in the drilling fluid.

2. The system of claim 1, further comprising a plurality of chambers that store the taggants.

3. The system of claim 2, wherein the processor processes the instructions of the taggant analysis and control engine and sends control signals to the taggant injection pump to release the taggants from the plurality of chambers.

4. The system of claim 3, wherein the processor sends the control signals to the taggant injection pump via a network connection.

5. The system of claim 3, wherein the processor directly interfaces with the taggant injection pump.

6. The system of claim 3, wherein the taggant injection pump comprises a plurality of release controls that are configured to release, in response to the control signals, the taggants from the plurality of chambers.

7. The system in claim 6,
wherein the control signals control a degree of shutting and opening of each of the plurality of release controls, and
wherein the control signals control an injection pressure at each of the plurality of release controls.

8. The system of claim 7, wherein the degree of shutting and opening of the plurality of release controls, and the injection pressure at the plurality of release controls are controlled by the control signals separately.

9. The system of claim 8, wherein the taggant injection pump comprises a plurality of sensors for measuring an injection volume and an injection flow rate.

10. The system of claim 9, wherein the taggant injection pump is a metered pump configured to inject a measured injection volume of the taggants into the drilling fluid.

11. The system of claim 1, wherein the taggant analysis and control engine optimizes a volume and an injection pressure of the injected taggants.

12. The system of claim 1, wherein the taggant analysis and control engine is located on a server and communicates with the processor via a network connection.

13. A method for drilling a wellbore, comprising:
generating, using a machine learning model and based on a drilling fluid parameter, a drilling parameter, and a formation parameter, to generate an injection profile;
controlling, based on the injection profile, injection parameters of a taggant injection pump to improve a quality of rock cutting depth determination, wherein the taggant injection pump is in fluid communication with a circulation path for a drilling fluid;
releasing, using the taggant injection pump, taggants into the drilling fluid, wherein the taggants are transported downhole by the drilling fluid to impregnate rock cuttings as the rock cuttings are produced by a drill bit;
detecting, using a taggant detector in fluid communication with a return part of the circulation path, the taggants for determining a rock cutting depth of the rock cuttings,
wherein mud logging is performed based on an improved quality of the rock cutting depth determination, and
wherein a machine learning model is used to forecast, in real time, quantities and concentrations of the taggants detected in the drilling fluid.

14. The method of claim 13, wherein the injection parameters comprise a degree of shutting and opening of a plurality of release controls of the taggant injection pump, and an injection pressure at the plurality of release controls.

15. The method of claim 13, wherein the injection profile specifies an optimized quantity and injection pressure of the taggants released into the drilling fluid.

16. A non-transitory computer readable medium comprising program instructions, that when executed, are configured to perform a method rock cutting depth determination, the method comprising:
generating, using a machine learning model and based on a drilling fluid parameter, a drilling parameter, and a formation parameter, to generate an injection profile;
controlling, based on the injection profile, injection parameters of a taggant injection pump to improve a quality of rock cutting depth determination, wherein the taggant injection pump is in fluid communication with a circulation path for a drilling fluid;
releasing, using the taggant injection pump, taggants into the drilling fluid, wherein the taggants are transported downhole by the drilling fluid to impregnate rock cuttings as the rock cuttings are produced by a drill bit;
detecting, using a taggant detector in fluid communication with a return part of the circulation path, the taggants for determining a rock cutting depth of the rock cuttings,
wherein mud logging is performed based on an improved quality of the rock cutting depth determination, and
wherein a machine learning model is used to forecast, in real time, quantities and concentrations of the taggants detected in the drilling fluid.

17. The non-transitory computer readable medium 16, wherein the injection parameters comprise a degree of shutting and opening of a plurality of release controls of the taggant injection pump, and an injection pressure at the plurality of release controls.

18. The non-transitory computer readable medium 16, wherein the injection profile specifies an optimized quantity and injection pressure of the taggants released into the drilling fluid.

* * * * *